US010383328B2

(12) United States Patent
Vernay et al.

(10) Patent No.: US 10,383,328 B2
(45) Date of Patent: Aug. 20, 2019

(54) AGRICULTURAL ADJUVANT COMPOSITIONS OF OIL/SURFACTANT/SALT EMULSIONS AND METHODS FOR USE

(71) Applicants: Rhodia Operations, Paris (FR); Centre National de la Recherche Scientifique, Paris (FR); Université de Montpellier, Montpellier (FR)

(72) Inventors: Clara Vernay, Paris (FR); Rajesh Goyal, Gujarat (IN); Laurence Ramos, Montpellier (FR); Christian Ligoure, Montpellier (FR); Jean-Christophe Castaing, Sevres (FR)

(73) Assignees: Rhodia Operations, Paris (FR); Centre National de la Recherche Scientifique, Paris (FR); Université de Montpellier, Montpellier (FR)

( * ) Notice: Subject to any disclaimer, the term of this patent is extended or adjusted under 35 U.S.C. 154(b) by 0 days.

(21) Appl. No.: 15/210,184

(22) Filed: Jul. 14, 2016

(65) Prior Publication Data

US 2017/0013829 A1    Jan. 19, 2017

Related U.S. Application Data

(60) Provisional application No. 62/192,127, filed on Jul. 14, 2015.

(51) Int. Cl.
  *A01N 25/06* (2006.01)
  *A01N 25/30* (2006.01)
  *A01N 25/08* (2006.01)
  *A01N 25/04* (2006.01)
  *A01N 57/20* (2006.01)

(52) U.S. Cl.
  CPC ............ *A01N 25/06* (2013.01); *A01N 25/04* (2013.01); *A01N 25/08* (2013.01); *A01N 25/30* (2013.01)

(58) Field of Classification Search
  None
  See application file for complete search history.

(56) References Cited

U.S. PATENT DOCUMENTS

| | | | |
|---|---|---|---|
| 4,834,908 A | 5/1989 | Hazen et al. | |
| 5,874,096 A | 2/1999 | Hazen | |
| 6,214,771 B1 | 4/2001 | Dexter | |
| 2004/0077499 A1 | 4/2004 | Graham et al. | |
| 2004/0097372 A1* | 5/2004 | Abraham | A01N 57/20 504/127 |
| 2006/0094601 A1 | 5/2006 | Hazen et al. | |
| 2006/0183641 A1 | 8/2006 | Otsubo et al. | |
| 2010/0179228 A1 | 7/2010 | Vermeer et al. | |
| 2010/0304967 A1* | 12/2010 | Kotzian | A01N 25/00 504/105 |
| 2013/0123104 A1 | 5/2013 | McKnight et al. | |
| 2013/0252817 A1 | 9/2013 | Shao et al. | |
| 2014/0113827 A1 | 4/2014 | Goyal et al. | |
| 2014/0134270 A1 | 5/2014 | Wu et al. | |
| 2015/0051076 A1 | 2/2015 | Schnabel et al. | |
| 2015/0051077 A1 | 2/2015 | Schnabel et al. | |

FOREIGN PATENT DOCUMENTS

| | | |
|---|---|---|
| EP | 2777394 A1 | 11/2012 |
| WO | 199929171 A1 | 6/1999 |
| WO | 200067573 A1 | 11/2000 |
| WO | 2002091831 A | 11/2002 |
| WO | 2005002336 A1 | 1/2005 |
| WO | 2006127661 A1 | 10/2008 |
| WO | 2010037734 A2 | 4/2010 |
| WO | 2010051435 A2 | 5/2010 |
| WO | 2013040006 A1 | 3/2013 |
| WO | 2013043678 A1 | 3/2013 |

OTHER PUBLICATIONS

PCT Third Party Observation dated Apr. 14, 2017 for PCT/US2016/042268 to Solvay USA Inc. filed Jul. 14, 2016.

* cited by examiner

*Primary Examiner* — John Pak
*Assistant Examiner* — Daniel L Branson
(74) *Attorney, Agent, or Firm* — Vorys, Sater, Seymour and Pease LLP

(57) ABSTRACT

An adjuvant composition that contains (a) one or more anionic surfactant compounds, (b) one or more one or more fatty acid alkyl ester compounds, and (c) one or more salts is useful as a component of pesticide compositions.

26 Claims, 2 Drawing Sheets

AGRICULTURAL ADJUVANT COMPOSITIONS OF OIL/SURFACTANT/SALT EMULSIONS AND METHODS FOR USE

CROSS REFERENCE TO RELATED APPLICATIONS

This application claims the benefit of U.S. Provisional Patent Application No. 62/192,127 filed Jul. 14, 2015, incorporated herein by reference in its entirety.

FIELD OF THE INVENTION

This invention relates to agricultural adjuvant compositions, pesticide compositions and methods for using such compositions, and in particular to adjuvant compositions useful in providing anti-drift properties.

BACKGROUND OF THE INVENTION

Many agricultural pesticides, including insecticides, fungicides, herbicides, miticides, and plant growth regulators, are applied in the form of a liquid composition. In addition to the pesticide and a solvent, such liquid compositions typically include one or more adjuvant compounds which are intended to improve one or more properties of the liquid composition, such as for example, storage stability, ease of handling, pesticide efficacy against target organisms, including anti-drift.

There is a continuing interest in adjuvant compositions and pesticide compositions that exhibit improved properties.

SUMMARY OF THE INVENTION

In a first aspect, the present invention is directed to an adjuvant composition comprising, (a) one or more anionic surfactant compounds;
(b) one or more fatty acid alkyl ester compounds; and
(c) one or more salts.

In a second aspect, the present invention is directed to a pesticide composition, comprising:
(a) one or more anionic surfactant compounds,
(b) one or more fatty acid alkyl ester compounds,
(c) one or more salts; and
(c) an effective amount of a pesticide.

In a third aspect, the present invention is directed to a tank solution, comprising:
(a) an adjuvant composition comprising:
i. one or more anionic surfactant compounds,
ii. one or more fatty acid alkyl ester compounds, and
iii. one or more salts;
(b) water; and
(c) an effective amount of a pesticide;
wherein the adjuvant composition is present in the tank solution in an amount from about 1 g/L to about 100 g/L.

In some embodiments, the adjuvant is present in the tank solution in an amount from about 1 g/L to about 75 g/L, or from 1 g/L to about 50 g/L, 1 g/L to about 35 g/L, or from 1 g/L to about 25 g/L, 1 g/L to about 20 g/L.

In other embodiments, the adjuvant is present in the tank solution in an amount from about 5 g/L to about 100 g/L, from about 10 g/L to about 100 g/L, or from about 15 g/L to about 100 g/L, or from about 20 g/L to about 100 g/L, from about 25 g/L to about 100 g/L.

In a third aspect, the present invention is directed to a method for treating a target plant, comprising applying the above described pesticide composition to such plant.

In a fourth aspect, the present invention is directed to a method to prepare a tank solution comprising the step of contacting an adjuvant composition, the adjuvant composition comprising:
one or more anionic surfactant compounds,
one or more fatty acid alkyl ester compounds, and
one or more salts;
with an aqueous solution comprising an effective amount of pesticide.

DETAILED DESCRIPTION OF INVENTION AND PREFERRED EMBODIMENTS

Figure 1:
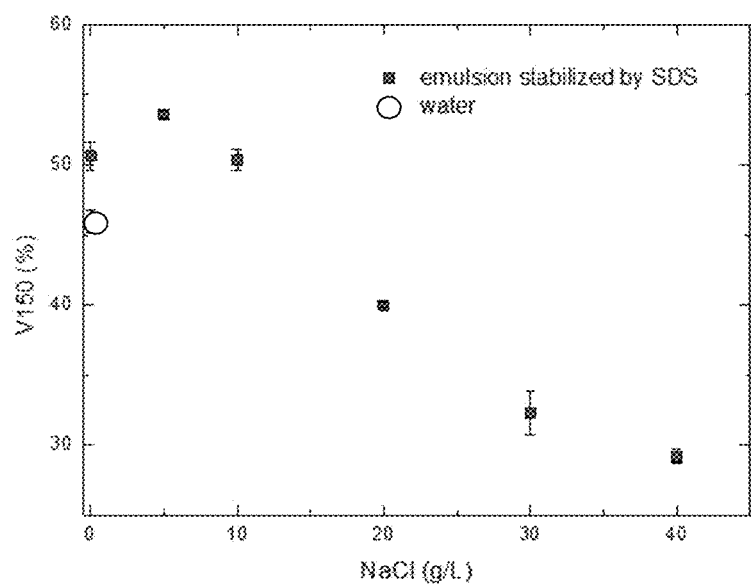
FIG. 1 is a graph of V150 (% of volume of spray fines below 150 microns (representative of driftable fines) averaged over the center of the spray fan as a function of salt amount (g/L) to illustrate the effect of salt on drift reduction performance.
Figure 2:
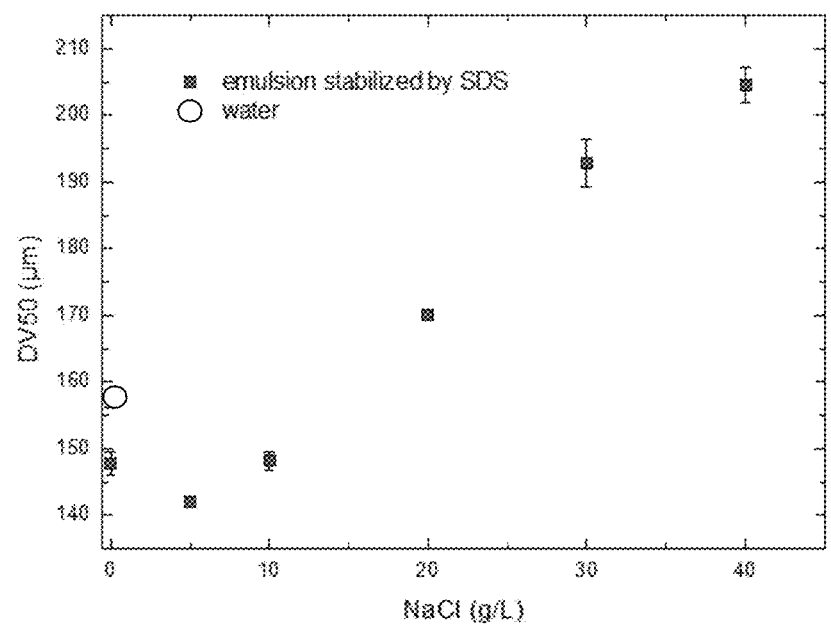
FIG. 2 is a graph of DV50 (defined as the droplet size below which 50% volume of spray is contained) averaged over the center of the spray fan as a function of salt amount (g/L) to illustrate the effect of salt on drift reduction performance.

As used herein, the term "alkyl" means a saturated straight chain, branched chain, or cyclic hydrocarbon radical, such as for example, methyl, ethyl, n-propyl, iso-propyl, n-butyl, sec-butyl, t-butyl, pentyl, n-hexyl, and cyclohexyl.

As used herein, the term "alkoxy" means an oxy radical that is substituted with an alkyl group, such as for example, methoxy, ethoxy, propoxy, isopropoxy, and butoxy. As used herein in reference to an organic compound, the term "alkoxylated" means that the compound comprises one or more alkoxy or, more typically, poly(alkyleneoxy) moieties, such as, for example a poly(ethyleneoxy), poly(propyleneoxy), or poly(ethlyeneoxypropyleneoxy) moiety and the term "ethoxylated" means that the compound comprises at least one ethoxy or poly(ethyleneoxy) moiety. As used herein in reference to a poly(alkyleneoxy) moiety, the notation "(n)", wherein n is an integer, indicates the number of alkyleneoxy monomeric units in the poly(alkyleneoxy) moiety. For example such as "ethoxylated (15) tridecyl alcohol" means a tridecyl alcohol ethoxylated with 15 moles of ethyleneoxy units per mole of tridecyl alcohol.

As used herein, the term "alkenyl" means an unsaturated straight chain, branched chain, or cyclic hydrocarbon radical that contains one or more carbon-carbon double bonds, such as, for example, ethenyl, 1-propenyl, and 2-propenyl.

As used herein, the term "aryl" means a monovalent unsaturated hydrocarbon radical containing one or more six-membered carbon rings in which the unsaturation may be represented by three conjugated double bonds, which may be substituted one or more of carbons of the ring with hydroxy, alkyl, alkenyl, halo, haloalkyl, or amino, such as, for example, phenoxy, phenyl, methylphenyl, dimethylphenyl, trimethylphenyl, chlorophenyl, trichloromethylphenyl, aminophenyl, and tristyrylphenyl.

As used herein, the term "arylene" means a divalent unsaturated hydrocarbon radical containing one or more six-membered carbon rings in which the unsaturation may be represented by three conjugated double bonds, which may be substituted one or more of carbons of the ring with hydroxy, alkyl, alkenyl, halo, haloalkyl, or amino, such as, for example, phenylene, methylphenylene, trimethylphenylene, aminophenylene, and tristyrylphenylene.

As used herein, the term "aralkyl" means an alkyl group substituted with one or more aryl groups, such as, for example, phenylmethyl, phenylethyl, and triphenylmethyl.

As used herein, the term "aralkenyl" means an alkenyl group substituted with an aryl group, such as, for example, phenylethenyl, and phenylpropenyl.

As used herein, the term "aryloxy" means an oxygen radical substituted with an aryl group, such as, for example, phenoxy, methylphenoxy, and trimethylphenoxy.

As used herein, the terminology "$(C_n\text{-}C_m)$" in reference to an organic group, wherein n and m are each integers, indicates that the group may contain from n carbon atoms to m carbon atoms per group.

As used herein, the term "agronomically acceptable salts" refers to salts prepared from agronomically acceptable non-toxic bases or acids including inorganic or organic bases and inorganic or organic acids. Typical agronomically acceptable salts the compound referred to herein comprise an anion derived from the compound, for example, by deprotonation of a hydroxy or hydroxyalkyl substituent, and one or more positively charged counterions. Suitable positively charged counterions include inorganic cations and organic cations, such as for example, sodium cations, potassium cations, calcium cations, magnesium cations, isopropylamine cations, ammonium cations, and tetraalkylammonium cations.

In one embodiment, described herein are adjuvant compositions comprising,
(a) one or more anionic surfactant compounds;
(b) one or more fatty acid alkyl ester compounds; and
(c) one or more salts.

In another embodiment, described herein are pesticide compositions comprising:
(a) one or more anionic surfactant compounds,
(b) one or more fatty acid alkyl ester compounds,
(c) one or more salts; and
(d) an effective amount of a pesticide.

The pesticide composition can be concentrated pesticide composition containing no or little water, generally less than 10 wt % (by total weight). In another embodiment, the concentrated pesticide composition contains less than 5 wt % of water (by total weight). In yet another embodiment, the concentrated pesticide composition contains less than 1 wt % of water (by total weight of composition).

In another embodiment, the present invention is directed to a tank solution, comprising:
(a) an adjuvant composition comprising:
  i. one or more anionic surfactant compounds,
  ii. one or more fatty acid alkyl ester compounds, and
  iii. one or more salts;
(b) water; and
(c) an effective amount of a pesticide;
wherein the adjuvant composition is present in the tank solution in an amount from about 1 g/L to about 100 g/L.

In some embodiments, the adjuvant is present in the tank solution in an amount from about 1 g/L to about 75 g/L, or from 1 g/L to about 50 g/L, 1 g/L to about 35 g/L, or from 1 g/L to about 25 g/L, 1 g/L to about 20 g/L.

In other embodiments, the adjuvant is present in the tank solution in an amount from about 5 g/L to about 100 g/L, from about 10 g/L to about 100 g/L, or from about 15 g/L to about 100 g/L, or from about 20 g/L to about 100 g/L, from about 25 g/L to about 100 g/L.

In one embodiment, the one or more fatty acid alkyl ester compounds is present in an amount of between about 0.01 wt % to about 10 wt %, by weight of the adjuvant composition. In one embodiment, the one or more fatty acid alkyl ester compounds is present in an amount of between about 0.01 wt % to about 20 wt %, by weight of the adjuvant composition. In another embodiment, the one or more fatty acid alkyl ester compounds is present in an amount of between about 1 wt % to about 50 wt %, by weight of the adjuvant composition. In another embodiment, the one or more fatty acid alkyl ester compounds is present in an amount of between about 2 wt % to about 30 wt %, by weight of the adjuvant composition. In another embodiment, the one or more fatty acid alkyl ester compounds is present in an amount of between about 4 wt % to about 20 wt %, by weight of the adjuvant composition. In another embodiment, the one or more fatty acid alkyl ester compounds is present in an amount of between about 7 wt % to about 15 wt %, by weight of the adjuvant composition.

In one embodiment, the one or more anionic surfactants is present in an amount of between about 0.1 wt % to about 10 wt %, by weight of the adjuvant composition. In one embodiment, the one or more anionic surfactants is present in an amount of between about 0.1 wt % to about 20 wt %, by weight of the adjuvant composition. In one embodiment, the one or more anionic surfactants is present in an amount of between about 1 wt % to about 99 wt %, by weight of the adjuvant composition. In another embodiment, the one or more anionic surfactants is present in an amount of between about 5 wt % to about 80 wt %, by weight of the adjuvant composition. In another embodiment, the one or more anionic surfactants is present in an amount of between about 7 wt % to about 40 wt %, by weight of the adjuvant composition. In another embodiment, the one or more anionic surfactants is present in an amount of between about 8 wt % to about 20 wt %, by weight of the adjuvant composition.

In one embodiment, the one or more salts is present in an amount of between about 50 wt % to about 90 wt %, by weight of the adjuvant composition. In another embodiment, the one or more salts is present in an amount of between about 60 wt % to about 99 wt %, by weight of the adjuvant composition. In another embodiment, the one or more salts is present in an amount of between about 70 wt % to about 95 wt %, by weight of the adjuvant composition. In another embodiment, the one or more salts is present in an amount of between about 75 wt % to about 95 wt %, by weight of the adjuvant composition.

Described herein are also methods to prepare a tank solution comprising the step of contacting an adjuvant composition, the adjuvant composition comprising:
  one or more anionic surfactant compounds,
  one or more fatty acid alkyl ester compounds, and
  one or more salts;
with an aqueous solution comprising an effective amount of pesticide.

The adjuvant composition can be contacted with the aqueous solution in one mix, or in successive steps. For example, the anionic surfactant compounds, can first be added to the aqueous solution (of water and pesticide), then the one or more fatty acid alkyl ester compounds can be added to the aqueous solution, then finally the one or more salts comprising the adjuvant composition is added to the aqueous solution. As another example, a part, portion or percentage of the adjuvant is contacted with the aqueous solution, followed by successive adjuvant addition steps (of a part, portion or percentage of the adjuvant composition)

until all adjuvant composition is contacted with the aqueous solution. Contacting includes, but is not limited to, mixing, dispersing, stirring, agitating and the like. It is understood that the adjuvant composition component can be added in any conceivable successive order or in any conceivable successive amount to the aqueous solution. In another embodiment, the pesticide is added to the aqueous solution after or concurrently with the addition of the adjuvant composition.

In another embodiment, described herein are methods for preparing the adjuvant or pesticide compositions described herein, such methods comprising contacting (a) one or more anionic surfactant compounds, (b) one or more fatty acid alkyl ester compounds, and (c) one or more salts with each other to prepare an adjuvant composition. In the case of the pesticide composition, such method to prepare the pesticide composition comprises contacting (i) an effective amount of a pesticide with (ii) a mixture of: (iia) one or more anionic surfactant compounds, (iib) one or more fatty acid alkyl ester compounds, and (iic) one or more salts.

In yet another embodiment, described herein treating a target plant, comprising applying the above described pesticide composition to such plant.

In some embodiments, the anionic surfactant compound includes one or more of, for example, linear alkylbenzene sulfonates, alpha olefin sulfonates, paraffin sulfonates, alkyl ester sulfonates, alkyl sulfates, alkyl alkoxy sulfates, alkyl sulfonates, alkyl alkoxy carboxylates, alkyl alkoxylated sulfates, alkyl aryl ether sulfates, diphenylene oxide disulfonates, alkyl napthalene sulfonates, monoalkyl(ether) phosphates, dialkyl(ether) phosphates, sarcosinates, sulfosuccinates, isethionates, and taurates, as well as mixtures thereof.

Other anionic surfactants that are suitable as the anionic surfactant compound include, for example, ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate (also referred to herein as sodium dodecyl sulfate), sodium laureth sulfate, potassium lauryl sulfate, potassium laureth sulfate, sodium lauryl phosphate, sodium tridecyl phosphate, sodium behenyl phosphate, sodium laureth-2 phosphate, sodium ceteth-3 phosphate, sodium trideceth-4 phosphate, sodium dilauryl phosphate, sodium ditridecyl phosphate, sodium ditrideceth-6 phosphate, sodium lauroyl sarcosinate, lauroyl sarcosine, cocoyl sarcosine, ammonium cocyl sulfate, ammonium lauryl sulfate, sodium cocyl sulfate, sodium trideceth sulfate, sodium tridecyl sulfate, ammonium trideceth sulfate, ammonium tridecyl sulfate, sodium cocoyl isethionate, disodium laureth sulfosuccinate, sodium methyl oleoyl taurate, sodium laureth carboxylate, sodium trideceth carboxylate, sodium lauryl sulfate, potassium cocyl sulfate, potassium lauryl sulfate, monoethanolamine cocyl sulfate, sodium tridecyl benzene sulfonate, and sodium dodecyl benzene sulfonate.

Branched anionic surfactants, in another embodiment can be utilized as the anionic surfactant compound, which include but is not limited to, sodium trideceth sulfate, sodium tridecyl sulfate, ammonium trideceth sulfate, ammonium tridecyl sulfate, and sodium trideceth carboxylate.

In another embodiment, anionic surfactant compounds include sulfonate surfactant compounds such as, for example, calcium dodecylbenzene sulfonate, calcium octadecylphenyl sulfonate, sodium tridecyl benzene sulfonate, isopropylamine dodecyl benzene sulfonate, isopropylamine tridecyl benzene sulfonate, ammonium tridecyl phenyl sulfonate, sodium $(C_8-C_{18})$alkylphenoxysulfonate, sodium xylene sulfonate, sodium $(C_{14}-C_{16})$alpha olefin sulfonate and mixtures thereof.

In another embodiment, anionic surfactant compounds include sulfosuccinate surfactant compounds such as agronomically acceptable salts of mono-esters of sulfosuccinic acid, agronomically acceptable salts of di-esters of sulfosuccinic acid, each of which may, optionally, be alkoxylated, as well as mixtures thereof. In one embodiment, the adjuvant composition comprises one or more sulfosuccinate surfactant compounds according to formula (V):

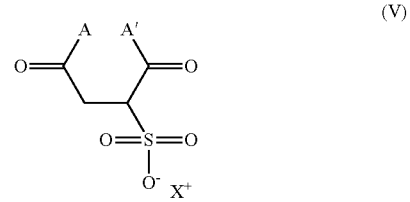

wherein:

A and A' are each independently —O⁻X⁺, or

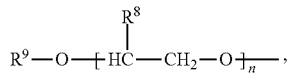

provided that at least one of A and A' is

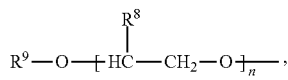

each $R^8$ is independently H or methyl, each $R^9$ is independently H, alkyl, aryl, or alkylamidoalkyl, each n is independently 0 or an integer of from 1 to about 100, more typically from 1 to 50, and each $X^+$ is an agronomically acceptable cation.

In one embodiment, one of A and A' is —O⁻X⁺, and the other of A and A' is

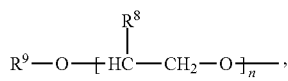

wherein n is 0 or an integer of from 1 to about 20, and $R^9$ is $(C_6-C_{18})$alkyl, $(C_1-C_{18})$alkylphenyl, or $(C_6-C_{18})$alkylamido$(C_2-C_6)$alkyl.

In one embodiment, A and A' are each

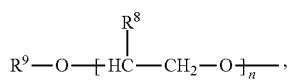

wherein each n is independently 0 or an integer of from 1 to about 20, and each $R^9$ is $(C_6-C_{18})$alkyl, $(C_1-C_{18})$alkylphenyl, or $(C_6-C_{18})$alkylamido$(C_2-C_6)$alkyl.

In another embodiment, sulfosuccinate surfactant compounds include, for example, disodium monooctylsulfosuccinate, sodium dioctylsulfosuccinate, disodium lauryl sulfosuccinate, disodium laureth sulfosuccinate, disodium laurimide (MEA) sulfosuccinate, disodium mono-alkylphenyl ether sulfosuccinate, and mixtures thereof.

Suitable fatty acid alkyl ester compounds include, in one embodiment, fatty acid methyl esters derived from lauric acid or isostearic acid. In one embodiment, the fatty acid alkyl ester is methyl laurate (lauric acid methyl ester). Suitable fatty acid alkyl esters include, in other embodiments, fatty acid methyl esters derived from caprylic acid, capric acid, myristic acid, palmitic acid, stearic acid, arachidic acid, behenic acid, lignoceric acid, or cerotic acid.

Fatty acid alkyl esters can be prepared by any suitable methods known to persons skilled in the art. For example, a fatty acid alkyl ester can be obtained by trans-esterification of an alkyl alcohol with a monoglyceride, di-glyceride and tri-glyceride (i.e., fatty acid glycerides) which are components of vegetable oils, animal fats and used fats and oils of them.

In one embodiment, the salt is an inorganic salt. In other embodiments, the salt is sodium chloride. In yet another embodiment, the salt is selected from magnesium sulfate, magnesium oxide, magnesium carbonate, potassium carbonate, potassium bitartrate, potassium-sodium tartrate, potassium chloride, potassium bicarbonate, sodium glutamate, sodium citrate, sodium chloride and sodium bicarbonate. In another embodiment, the salt includes: sulfate, phosphate, formate, acetate, nitrate, citrate or chloride salts of ammonium. In another embodiment, the salt is selected from monopotassium phosphate, dipotassium hydrogen phosphate, tripotassium phosphate, potassium chloride, potassium sulfate, sodium sulfate or choline chloride.

In another embodiment, the salt is one or more acid salts, which includes but is not limited to sodium bicarbonate, sodium hydrosulfide, sodium bisulfate (NaHSO$_4$), monosodium phosphate (NaH$_2$PO$_4$), and disodium phosphate (Na$_2$HPO$_4$).

The adjuvant composition, in one embodiment, comprises a non-zero amount of the one or more anionic surfactant compounds, a non-zero amount of one or more fatty acid alkyl ester compounds, and a non-zero amount of one or more salts. As used herein, "non-zero amount" means an amount greater than 0.

In one embodiment, the adjuvant composition comprises, based on 100 parts by weight ("pbw") of the adjuvant composition:
(a) greater or equal to than about 0.1 pbw, more typically from about 1 pbw to about 99 pbw, even more typically from about 1 pbw to about 50 pbw, and still more typically from about 5 pbw to about 25 pbw, of one or more anionic surfactant compounds,
(b) greater or equal to than about 0.1 pbw, more typically from about 1 pbw to about 99 pbw, even more typically from about 1 pbw to about 50 pbw, and still more typically from about 5 pbw to about 25 pbw, of one or more fatty acid alkyl ester compounds; and
(c) greater or equal to than about 0.1 pbw, more typically from about 1 pbw to about 99 pbw, even more typically from about 30 pbw to about 95 pbw, and still more typically from about 40 pbw to about 90 pbw of one or more salts.

In one embodiment of the adjuvant composition, the one or more anionic surfactants comprise at least one alkyl sulfate surfactant or alkyl ether sulfate surfactant and may optionally further comprise one or more surfactants selected from sulfonates, sulfosuccinates, or alkyl ether carboxylates.

In one embodiment of the adjuvant composition, the one or more surfactants comprise at least one sulfosuccinate surfactant and may optionally further comprise one or more surfactants selected from alkyl ether sulfates, alkyl sulfates, sulfonates, or alkyl ether carboxylates.

In one embodiment, the pesticide or adjuvant composition comprises, per 1 pbw anionic surfactant component of such adjuvant composition, from about 0.1 to about 10, more typically from about 0.3 to about 8, more typically from about 0.5 to about 2 pbw, more typically from about 0.8 to about 1.5 pbw, more typically from about 0.8 to about 1.2 pbw, even more typically from about 0.9 to about 1.1 pbw of one or more fatty acid alkyl ester compounds.

In one embodiment, the pesticide or adjuvant composition comprises, per 1 pbw fatty acid alkyl ester compound component of such adjuvant composition, from about 0.1 to about 10, more typically from about 0.3 to about 8, more typically from about 0.5 to about 2 pbw, more typically from about 0.8 to about 1.5 pbw, more typically from about 0.8 to about 1.2 pbw, even more typically from about 0.9 to about 1.1 pbw of one or more anionic surfactant component.

In one embodiment, the pesticide or adjuvant composition comprises, per 1 pbw anionic surfactant compounds of such adjuvant composition, from about 0.1 to about 10, more typically from about 0.3 to about 8, more typically from about 0.5 to about 2 pbw, more typically from about 0.8 to about 1.5 pbw, more typically from about 0.8 to about 1.2 pbw, even more typically from about 0.9 to about 1.1 pbw of the mixture of one or more fatty acid alkyl ester compounds and one or more salts.

In one embodiment, the pesticide or adjuvant composition comprises, per 0.01 pbw fatty acid alkyl ester compounds of such adjuvant composition, from about 0.01 to about 0.20, more typically from about 0.03 to about 0.18, more typically from about 0.05 to about 0.15 pbw, more typically from about 0.06 to about 0.15 pbw, more typically from about 0.06 to about 0.12 pbw, even more typically from about 0.06 to about 0.11 pbw of the mixture of: (i) one or more anionic surfactant compounds and (ii) one or more salts.

In one embodiment, the pesticide or adjuvant composition comprises, (a) one or more anionic surfactant compounds; (b) one or more fatty acid alkyl ester compounds; (c) one or more salts, wherein wt % ratio of one or more anionic surfactant compounds to one or more fatty acid alkyl ester compounds is in the range of from about 1:2 to about 2:1, or, in another embodiment, is in the range of from about 1:1.7 to about 1.7:1, or, in another embodiment, is in the range of from about 1:1.5 to about 1.5:1, or, in yet another embodiment, is in the range of from about 1:1.2 to about 1.2:1, or, in a further embodiment, is in the range of from about 1:1.1 to about 1.1:1, respectively.

In an alternative embodiment, the ratio of one or more anionic surfactant compounds to one or more fatty acid alkyl ester compounds is in the range of from about 1:5 to about 5:1, respectively, or, in another embodiment, is in the range of from about 1:4 to about 4:1, respectively, or, in another embodiment, is in the range of from about 1:3.5 to about 3.5:1, respectively, or, in another embodiment, is in the range of from about 1:3 to about 3:1, respectively, or, in another embodiment, is in the range of from about 1:2.5 to about 2.5:1, respectively, or, in another embodiment, is in the range of from about 1:2 to about 2:1, respectively, or, in another embodiment, is in the range of from about 1:1.9 to about 1.9:1, respectively, or, in another embodiment, is in the range of from about 1:1.7 to about 1.7:1, respectively, or, in another embodiment, is in the range of from about 1:1.5 to about 1.5:1, respectively, or, in another embodiment, is in the range of from about 1:1.2 to about 1.2:1, respectively, or, in another embodiment, is in the range of from about 1:1.1 to about 1.1:1, respectively, or, in another embodiment, is in the range of from about 1:1.05 to about 1.05:1, respectively.

In one embodiment, the pesticide or adjuvant composition comprises, (a) one or more anionic surfactant compounds; (b) one or more fatty acid alkyl ester compounds; (c) one or more salts, wherein wt % ratio of (i) one or more fatty acid alkyl ester compounds to (ii) a mixture of one or more anionic surfactant compounds and one or more salts, respectively, is in the range of from about 1:5 to about 1:25, or, in another embodiment, is in the range of from about 1:5 to about 1:20, or, in another embodiment, is in the range of from about 1:6 to about 1:20, or, in yet another embodiment, is in the range of from about 1:7 to about 1:18, or, in a further embodiment, is in the range of from about 1:9 to about 1:16, respectively.

In an alternative embodiment, the wt % ratio of (i) one or more fatty acid alkyl ester compounds to (ii) a mixture of one or more anionic surfactant compounds and one or more salts, respectively, is in the range of from about 1:3 to about 1:40, respectively, or, in another embodiment, is in the range of from about 1:5 to about 1:25, respectively, or, in another embodiment, is in the range of from about 1:7 to about 1:20, respectively, or, in another embodiment, is in the range of from about 1:7 to about 1:17, respectively, or, in another embodiment, is in the range of from about 1:8 to about 1:17, respectively, or, in another embodiment, is in the range of from about 1:8 to about 1:16, respectively, or, in another embodiment, is in the range of from about 1:7 to about 1:16, respectively, or, in another embodiment, is in the range of from about 1:9 to about 1:18, respectively, or, in another embodiment, is in the range of from about 1:9 to about 1:17, respectively, or, in another embodiment, is in the range of from about 1:9 to about 1:16, respectively, or, in another embodiment, is in the range of from about 1:9 to about 1:15, respectively.

Suitable pesticides are biologically active compounds used to control agricultural pests and include, for example, herbicides, plant growth regulators, crop dessicants, fungicides, bacteriocides, bacteriostats, insecticides, and insect repellents. Suitable pesticides include, for example, triazine herbicides such as metribuzin, hexaxinone, or atrazine; sulfonylurea herbicides such as chlorsulfuron; uracils such as lenacil, bromacil, or terbacil, urea herbicides such as linuron, diuron, siduron, or neburon; acetanilide herbicides such as alachlor, or metolachlor; thiocarbamate herbicides such as benthiocarb, triallate; oxadiazolone herbicides such as oxadiazon; phenoxyacetic acids such as 2,4-D; diphenyl ether herbicides such as fluazifop, acifluorfen, bifenox, or oxyfluorfen; dinitro aniline herbicides such as trifluralin; organophosphonate herbicides such as glyphosate salts and esters; dihalobenzonitrile herbicides such as bromoxynil, or ioxynil, dipyridilium herbicides such as paraquat. Suitable fungicides include, for example, nitrilo oxime fungicides such as cymoxanil; imidazole fungicides such as benomyl, carbendazim, or thiophanate-methyl; triazole fungicides such as triadimefon; sulfenamide fungicides, such as captan; dithio-carbamate fungicides such as maneb, mancozeb, or thiram; chlorinated aromatic fungicides such as chloroneb; dichloro aniline fungicides such as iprodione, strobilurin fungicides such as kresoxim-methyl, trifloxystrobin or azox-ystrobin; chlorothalonil, copper salt fungicides such as copper oxychloride; sulfur; phenylamides; and acylamino fungicides such as metalaxyl or mefenoxam. Suitable insecticides, include, for example, carbamate insecticides, such as methomyl, carbaryl, carbofuran, or aldicarb; organo thiophosphate insecticides such as EPN, isofenphos, isoxathion, chlorpyrifos, or chlormephos; organophosphate insecticides such as terbufos, monocrotophos, or terachlorvinphos; perchlorinated organic insecticides such as methoxychlor; synthetic pyrethroid insecticides such as fenvalerate, abamectin or emamectin benzoate, neonicotinoide insecticides such as thiamethoxam or imidacloprid; pyrethroid insecticides such as lambda-cyhalothrin, cypermethrin or bifenthrin, and oxadiazine insecticides such as indoxacarb, imidachlopryd, or fipronil. Suitable miticides include, for example, propynyl sulfite miticides such as propargite; triazapentadiene miticides such as amitraz; chlorinated aromatic miticides such as chlorobenzilate, or tetradifan; and dinitrophenol miticides such as binapacryl. Suitable nematicides include carbamate nematicides, such as oxamyl.

Pesticide compounds are, in general, referred herein to by the names assigned by the International Organization for Standardization (ISO). ISO common names may be cross-referenced to International Union of Pure and Applied Chemistry ("IUPAC") and Chemical Abstracts Service ("CAS") names through a number of sources such as, for example, the Compendium of Pesticide Common Names, which is available on-line at http://www.hclrss.demon-.co.uk/index.html.

In one embodiment, the pesticide comprises one or more compounds selected from group consisting of herbicides, plant growth regulators, crop dessicants, fungicides, bacteriocides, bacteriostats, insecticides, miticides, nematocides, and insect repellents.

In one embodiment, the pesticide comprises one or more compounds selected from the group consisting of glufosinate, glyphosate, water soluble glufosinate salts, water soluble glyphosate salts, and mixtures thereof, including, for example sodium, potassium, isopropyl amine, and ammonium salts.

In one embodiment, the pesticide comprises one or more compounds selected from the group consisting of the potassium salt of glyphosate, the sodium salt of glyphosate, the isopropyl amine salt of glyphosate, the ammonium salt of glyphosate.

Herbicidal compositions containing glyphosate or derivatives thereof are used to control a very wide variety of plants worldwide and can, when applied to the target plant in a herbicidally effective amount, reportedly control one or more target plant species of one or more of the following genera: *Abutilon, Amaranthus, Artemisia, Asclepias, Avena, Axonopus, Borreria, Brachiaria, Brassica, Bromus, Chenopodium, Cirsium, Commelina, Convolvulus, Cynodon, Cyperus, Digitaria, Echinochloa, Eleusine, Elymus, Equisetum, Erodium, Helianthus, Imperata, Ipomoea, Kochia, Lolium, Malva, Oryza, Ottochloa, Panicum, Paspalum, Phalaris, Phragmites, Polygonum, Portulaca, Pteridium, Pueraria, Rubus, Salsola, Setaria, Sida, Sinapis, Sorghum, Triticum, Typha, Ulex, Xanthium* and *Zea*, including annual broadleaf species such as, for example, velvetleaf (*Abutilon theophrasti*), pigweed (*Amaranthus* spp.), buttonweed (*Borreria* spp.), oilseed rape, canola, indian mustard, etc. (*Brassica* spp.), commelina (*Commelina* spp.), filaree (*Erodium* spp.), sunflower (*Helianthus* spp.), morningglory (*Ipomoea* spp.), kochia (*Kochia scoparia*), mallow (*Malva* spp.), wild buckwheat, smartweed, etc. (*Polygonum* spp.), purslane (*Portulaca* spp.), russian thistle (*Salsola* spp.), *sida* (*Sida* spp.), wild mustard (*Sinapis arvensis*) and cocklebur (*Xanthium* spp.), annual narrowleaf species such as for example, wild oat (*Avena fatua*), carpetgrass (*Axonopus* spp.), downy brome (*Bromus tectorum*), crabgrass (*Digitaria* spp.), barnyardgrass (*Echinochloa crusgalli*), goosegrass (*Eleusine indica*), annual ryegrass (*Lolium multiflorum*), rice (*Oryza sativa*), ottochloa (*Ottochloa nodosa*), bahiagrass (*Paspalum notatum*), canarygrass (*Phalaris* spp.), foxtail (*Setaria* spp.), wheat (*Triticum aestivum*) and corn (*Zea mays*), perennial broadleaf species such as, for example, mugwort (*Artemisia* spp.), milkweed (*Asclepias* spp.), canada thistle (*Cirsium arvense*), field bindweed (*Convolvulus arvensis*) and kudzu (*Pueraria* spp.), perennial narrowleaf species such as for example, brachiaria (*Brachiaria* spp.), bermudagrass (*Cynodon dactylon*), yellow nutsedge (*Cyperus esculentus*), purple nutsedge (*C. rotundus*), quackgrass (*Elymus repens*), lalang (*Imperata cylindrica*), perennial ryegrass (*Lolium perenne*), guineagrass (*Panicum maximum*), dallisgrass (*Paspalum dilatatum*), reed (*Phragmites* spp.), johnsongrass (*Sorghum halepense*) and cattail (*Typha* spp.), and other perennial species such as, for example, horsetail (*Equisetum* spp.), bracken (*Pteridium aquilinum*), blackberry (*Rubus* spp.), and gorse (*Ulex europaeus*).

As used herein, the terminology "effective amount" in reference to the relative amount of a pesticide in a pesticide composition means the relative amount of pesticide that is effective to control the growth of a target organism, for example, a target plant, fungus, bacterium, or insect, when the pesticide composition is applied to the organism at a given application rate.

In one embodiment, the pesticide is glyphosate herbicide and the pesticide composition is an herbicide composition that comprises a herbicidally effective amount of glyphosate.

As used herein, the terminology "an herbicidally effective amount" in reference to the relative amount of herbicide in an herbicidal composition means the relative amount that is effective to control growth of a target plant when the herbicidal composition is spray applied to the target plant at a given application rate.

The adjuvant composition comprises a non-zero amount of the one or more surfactant compounds and a non-zero amount of one or more fatty acid alkyl ester compounds and a non-zero amount of one or more salts.

In one embodiment, the pesticide composition comprises, based on 100 pbw of the adjuvant composition:
(a) greater than or equal to about 0.001 part by weight, more typically from about 0.001 pbw to about 0.1 pbw, even more typically from about 0.005 pbw to about 0.095 pbw, and still more typically from about 0.02 pbw to about 0.08 pbw, of one or more anionic surfactant compounds,
(b) greater than or equal to about 0.001 part by weight, more typically from about 0.001 pbw to about 0.1 pbw, even more typically from about 0.005 pbw to about 0.095 pbw, and still more typically from about 0.02 pbw to about 0.08 pbw, of one or more fatty acid alkyl ester compounds,
(c) greater than or equal to about 0.1 part by weight, more typically from about 0.2 pbw to about 0.99 pbw, even more typically from about 0.5 pbw to about 0.95 pbw, and still more typically from about 0.6 pbw to about 0.9 pbw, of one or more salts, and
(d) an effective amount of a pesticide.

In one embodiment of the pesticide composition, the one or more anionic surfactant compounds comprise at least one alkyl sulfate surfactant and may optionally further comprise one or more surfactants selected from sulfonates, sulfosuccinates, or alkyl ether carboxylates.

In one embodiment of the pesticide composition, the one or more anionic surfactant compounds comprise at least one sulfonate surfactant and may optionally further comprise one or more surfactants selected from alkyl ether sulfates, sulfosuccinates, or alkyl ether carboxylates.

In one embodiment of the pesticide composition, the one or more anionic surfactants comprise at least one sulfosuccinate surfactant and may optionally further comprise one or more surfactants selected from alkyl ether sulfates, sulfonates, or alkyl ether carboxylates.

In one embodiment, the pesticide composition comprises, based on 100 pbw of the composition, from about 10 pbw to about 90 pbw, more typically from about 30 to about 60 pbw, glyphosate.

The adjuvant and pesticide compositions of the present invention may each, optionally, further comprise one or more agronomically acceptable solvent. Suitable solvents include, for example, water, and organic solvents, such as for example, alkylated aromatic solvents, such as toluene or alkylated naphthalenes and mineral oil fractions, such as paraffinic hydrocarbons.

In one embodiment, the adjuvant composition of the present invention is an aqueous composition and thus comprises water.

In one embodiment, the pesticide composition of the present invention is an aqueous composition and thus comprises water.

In one embodiment, the adjuvant composition of the present invention further comprises, based on 100 pbw of such composition, up to about 25 pbw an organic solvent.

In one embodiment, the pesticide composition further comprises a fertilizer. Such fertilizers can provide the primary nutrients of nitrogen, phosphorus and/or potassium such as urea ammonium nitrate (30-0-0), 10-34-0, secondary nutrients sulfur, calcium, magnesium such as ammonium thiosulfate 12-0-0-26S, micronutrient fertilizers containing zinc, iron, molybdenum, copper, boron, chlorine, magnesium, for example 0-0-1 3%-S; 3%-Zn; 2%-Fe; 2%-Mn and mixtures thereof. In one embodiment, the pesticide composition comprises from about 85 to about 99 pbw, more typically from about 90 to about 99 pbw, and even more typically from about 93 to about 99 pbw, of a mixture of fertilizer and water.

In one embodiment, the pesticide composition of the present invention further comprises one or more water conditioners, such as for example, chelating agents, such as ethylenediamine tetraacetic acid, complexing agents such as ammonium sulfate, and pH adjusting agents, such as citric acid and polyacrylic acid.

In one embodiment, the pesticide composition of the present invention comprises, based on 100 pbw of such composition, from about 0.1 to about 3 pbw, more typically from about 0.7 to about 2.5 pbw, of one or more water conditioners, typically ammonium sulfate.

The pesticide composition of the present invention may, optionally, further comprise other ingredients, such as one or more additional surfactants, one or more thickeners, such as polysaccharide thickeners, and polyacrylamide thickeners, as well as antifoams, spreaders, and drift control agents.

The adjuvant composition of the present invention is made by combining and mixing the components of such composition.

The pesticide composition of the present invention is made by mixing the ingredients together. In one embodiment, the pesticide composition is made by combining and mixing the adjuvant composition of the present invention, a pesticide compound, and water. Alternatively, the pesticide composition is made by combining and mixing the separate components of the adjuvant composition, a pesticide, and water.

In one embodiment, the pesticide composition is spray applied to foliage of a target plant at a rate of from about 0.5 pint/acre to about 3 pints/acre, more typically from about 0.5 pint/acre to about 2.5 pints/acre.

EXAMPLES

Several Dilutions of methyl laurate (oil) and sodium dodecyl sulfate (anionic surfactant) with increased amount of sodium chloride (salt) were made in distilled water as follows: the aqueous phase is first prepared, then methyl laurate is added to make the emulsion. The components, in total, were present in the amount shown in Table 1 and the obtained solutions were mixed using an Ultraturrax high speed homogenizer at a speed of 6000 rotations per minute (RPM) for one minute. The resultant mixtures were sprayed at a pressure of 3 bars through a flat fan Teejet XR11003 nozzle. A Malvern Sprayec instrument was used to scan the entire spray pattern to determine the drop size distribution. Two parameters V150 (% of volume of spray fines below 150 microns (i.e., representative of driftable fines)) and DV50 (defined as the droplet size below which 50% volume of spray is contained), both averaged over the center of the spray fan, are presented in FIG. 1 and FIG. 2, respectively, to study effect of salt on drift reduction performance. We see that addition of a certain amount of salt decreases driftable fines and increases the DV50 value.

TABLE I

Composition of dilutions of Example 1

| Example # | Amount of oil in mL | Amount of surfactant in gm | Amount of salt in gm | Amount of DI water (Liter) |
|---|---|---|---|---|
| C-A | 0.0 | 0.0 | 0 | 1.0 |
| C-B | 3.0 | 2.5 | 0 | Balance to 1.0 |
| 1-A | 3.0 | 2.5 | 5 | Balance to 1.0 |
| 1-B | 3.0 | 2.5 | 10 | Balance to 1.0 |
| 1-C | 3.0 | 2.5 | 20 | Balance to 1.0 |
| 1-D | 3.0 | 2.5 | 30 | Balance to 1.0 |
| 1-E | 3.0 | 2.5 | 40 | Balance to 1.0 |

The invention claimed is:

1. An adjuvant composition comprising:

(a) one or more anionic surfactant compounds, wherein the one or more anionic surfactant compounds comprises at least one member of the group consisting of sodium dodecyl sulfate, sodium laureth sulfate, potassium lauryl sulfate, and potassium laureth sulfate;

(b) methyl laurate; and (c) one or more inorganic salts selected from the group consisting of sodium chloride, potassium chloride and a mixture thereof;

wherein the adjuvant composition comprises, based on 100 parts by weight of the adjuvant composition, 5 to 20 parts by weight (pbw) of the one or more anionic surfactant compounds, 5 to 20 pbw of methyl laurate, and 75 to 90 pbw of the one or more inorganic salts;

wherein the ratio (wt %, by weight of composition) of the one or more anionic surfactant compounds to the methyl laurate is in the range of from 1:1.2 to 1.2:1, respectively.

2. The composition of claim 1, wherein the one or more anionic surfactant compounds comprises sodium dodecyl sulfate, wherein the one or more inorganic salts are selected from the group consisting of sodium chloride and a mixture of sodium chloride and potassium chloride;

wherein the ratio (wt %, by weight of composition) of the one or more anionic surfactant compounds to the methyl laurate is in the range of from 1:1.1 to 1.1:1, respectively;

adjuvant composition comprises, based on 100 parts by weight of the adjuvant composition, 5 to 16.5 parts by weight (pbw) of the one or more anionic surfactant compounds, 5 to 17 pbw of methyl laurate, and 75 to 90 pbw of the one or more salts.

3. The composition of claim 1 wherein the one or more anionic surfactant compounds comprises sodium dodecyl sulfate.

4. The composition of claim 1, consisting of:

(a) the one or more anionic surfactant compounds;

(b) the methyl laurate; and (c) the sodium chloride and/or potassium chloride.

5. The composition of claim 1 wherein the one or more inorganic salts are selected from the group consisting of sodium chloride and a mixture of sodium chloride and potassium chloride.

6. An aqueous composition consisting of water and the adjuvant composition of claim 1, wherein the adjuvant composition consists of:

(a) the one or more anionic surfactant compounds;

(b) the methyl laurate; and (c) the sodium chloride.

7. The composition of claim 1 wherein the ratio (wt %, by weight of composition) of the one or more anionic surfactant compounds to the methyl laurate is in the range of from 1:1.1 to 1.1:1, respectively.

8. A pesticide composition comprising:

the adjuvant composition of claim 1; and an effective amount of a pesticide.

9. The composition of claim 8 wherein the pesticide compound comprises one or more compounds selected from glufosinate, glyphosate, water soluble glufosinate salts, and water soluble glyphosate salts.

10. The composition of claim 8 wherein the pesticide compound comprises one or more compounds selected from the group consisting of potassium salt of glyphosate, sodium salt of glyphosate, isopropyl amine salt of glyphosate, and ammonium salt of glyphosate.

11. The composition of claim 8 wherein one or more anionic surfactant compounds comprises sodium dodecyl sulfate.

12. The composition of claim 8, consisting of:

(a) the one or more anionic surfactant compounds, wherein the one or more anionic surfactant compounds consists of at least one member of the group consisting of sodium dodecyl sulfate, sodium laureth sulfate, potassium lauryl sulfate, and potassium laureth sulfate;

(b) the methyl laurate;

(c) the sodium chloride and/or potassium chloride; and (d) an effective amount of a pesticide.

13. The composition of claim 8 wherein one or more salts are selected from the group consisting of sodium chloride and a mixture of sodium chloride and potassium chloride.

14. A pesticide composition comprising:
the adjuvant composition of claim 2; and
an effective amount of a pesticide.

15. The composition of claim 8 wherein the ratio (wt %, by weight of composition) of one or more anionic surfactant compounds to methyl laurate is in the range of from 1:1.1 to 1.1:1, respectively.

16. A method for treating a target organism to control the growth of the organism, comprising applying to the organism a pesticide composition according to claim 8.

17. The method of claim 16 wherein the pesticide comprises one or more compounds selected from glufosinate, glyphosate, water soluble glufosinate salts, and water soluble glyphosate salts.

18. The composition of claim 16 wherein the pesticide compound comprises one or more compounds selected from the group consisting of potassium salt of glyphosate, sodium salt of glyphosate, isopropyl amine salt of glyphosate, and ammonium salt of glyphosate.

19. An agricultural tank solution comprising:
(a) an adjuvant composition of claim 1;
(b) water; and
(c) an effective amount of a pesticide;
wherein the adjuvant composition is present in the tank solution in an amount from about 1 g/L to about 100 g/L.

20. The tank solution of claim 19 wherein adjuvant is present in the tank solution in an amount from 1 g/L to about 50 g/L.

21. The tank solution of claim 19 wherein the methyl laurate is present in an amount of 5 to 17 pbw per 100 pbw of the adjuvant composition.

22. The tank solution of claim 19 wherein the one or more anionic surfactants is present in an amount of 5 to 16.5 pbw per 100 pbw of the adjuvant composition.

23. The tank solution of claim 19 wherein the one or more inorganic salts is present in an amount of about 80 to 90 pbw per 100 pbw of the adjuvant composition.

24. A method to prepare a tank solution comprising the step of contacting an adjuvant composition of claim 1 with an aqueous solution comprising an effective amount of pesticide.

25. The method of claim 24 wherein the one or more anionic surfactant compounds, methyl laurate, and one or more inorganic salts comprising the adjuvant composition are added to the aqueous solution in successive steps.

26. The method of claim 24 wherein,
(i) the methyl laurate is present in an amount of 5 to 17 pbw per 100 pbw of the adjuvant composition;
(ii) the one or more anionic surfactants is present in an amount of 5 to 16.5 pbw per 100 pbw of the adjuvant composition; and
(iii) the one or more inorganic salts is present in an amount about 80 to 90 pbw per 100 pbw of the adjuvant composition.

* * * * *